US00PP26701P3

(12) United States Plant Patent
Dobres

(10) Patent No.: US PP26,701 P3
(45) Date of Patent: May 3, 2016

(54) ***PENSTEMON* PLANT NAMED 'NOVAPENPIN'**

(50) Latin Name: *Penstemon barbatus*
Varietal Denomination: Novapenpin

(71) Applicant: CP DELAWARE, INC., Wilmington, DE (US)

(72) Inventor: Michael S. Dobres, Philadelphia, PA (US)

(73) Assignee: CP DELAWARE, INC., Wilmington, DE (US)

( * ) Notice: Subject to any disclaimer, the term of this patent is extended or adjusted under 35 U.S.C. 154(b) by 170 days.

(21) Appl. No.: 13/998,879

(22) Filed: Dec. 18, 2013

(65) Prior Publication Data

US 2015/0173289 P1 Jun. 18, 2015

(51) Int. Cl.
*A01H 5/02* (2006.01)

(52) U.S. Cl.
USPC ..... Plt./465

(58) Field of Classification Search
USPC ..... Plt./465
See application file for complete search history.

(56) References Cited

U.S. PATENT DOCUMENTS

| | | | |
|---|---|---|---|
| PP23,064 | P2 | 9/2012 | Lubbe |
| PP23,065 | P2 | 9/2012 | Lubbe |
| PP23,066 | P2 | 9/2012 | Lubbe |
| PP23,067 | P2 | 9/2012 | Lubbe |
| PP23,089 | P2 | 9/2012 | Lubbe |
| PP23,098 | P2 | 10/2012 | Lubbe |

*Primary Examiner* — Keith Robinson
(74) *Attorney, Agent, or Firm* — Buchanan Ingersoll & Rooney PC

(57) ABSTRACT

The new *Penstemon* plant was created by the crossing of parent plants which had been studied in the hope that they might provide desired characteristics. Attractive bright pink blossoms with a white throat are formed in the absence of a vernalization requirement for flowering. An upright compact mounding growth habit is displayed. The plant is well suited for providing attractive ornamentation in the landscape.

2 Drawing Sheets

Figure 1:
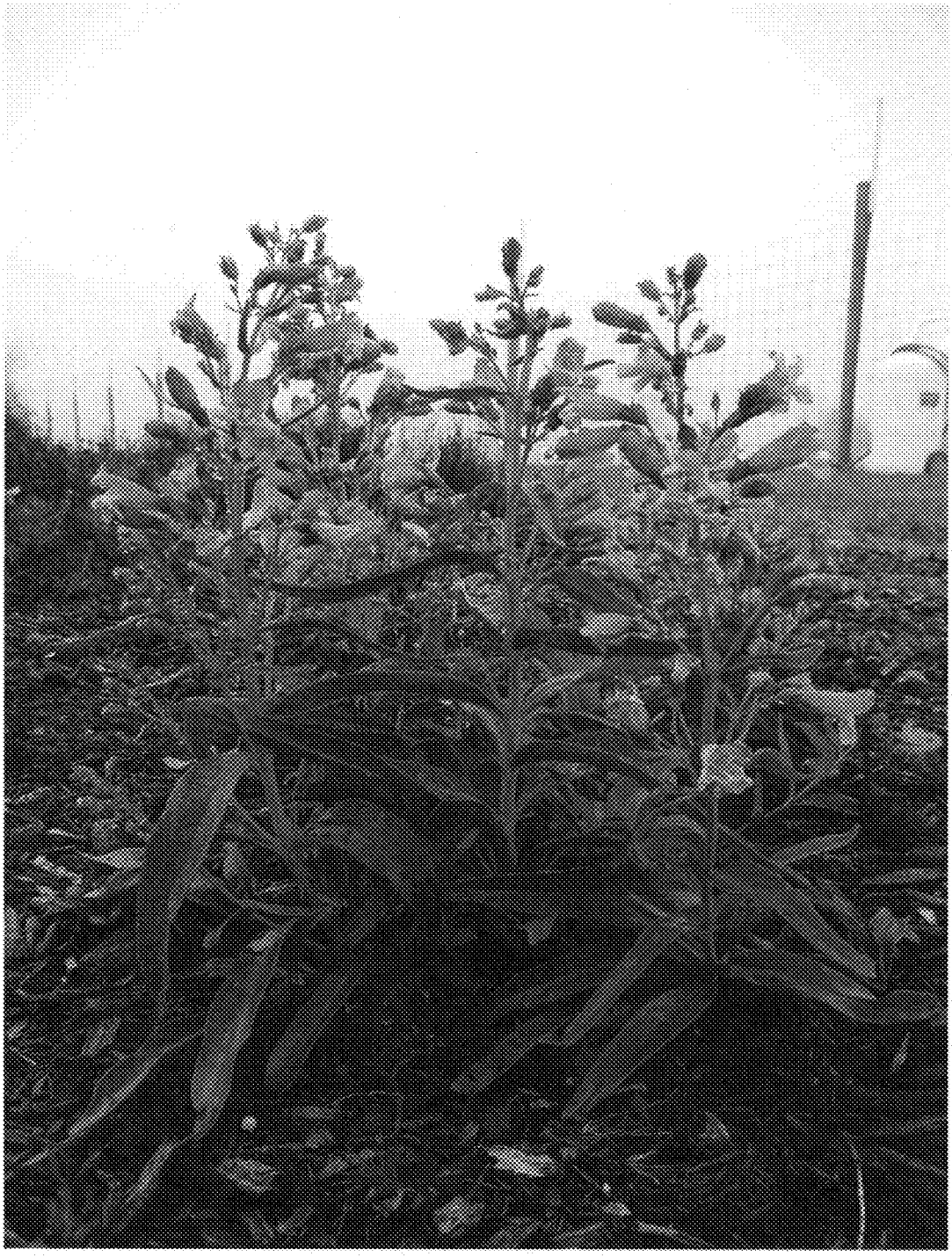

Botanical/commercial classification: *Penstemon barbatus/ Penstemon* Plant.

Varietal denomination: cv. Novapenpin.

SUMMARY OF THE INVENTION

*Penstemon* plants, sometimes known as Beard Tongue, are herbaceous perennials which provide colorful flowers during the summer.

The new *Penstemon* plant of the present invention was created at West Grove, Pa., U.S.A., by artificial pollination wherein two parents were crossed which previously had been studied in the hope that they would provide the desired characteristics. Each parent was acquired as a seed mixture. The female parent (i.e., seed parent) was *Penstemon barbatus* 'Rondo' (non-patented in the United States). The male parent (i.e., pollen parent) was *Penstemon barbatus* 'Navigator' (non-patented in the United States).

The parentage of the new variety can be summarized as follows:

'Rondo'×'Navigator'.

The seeds resulting from the above pollination were sown and small plants were obtained which were physically and biologically different from each other. Selective study resulted in the identification of a single plant of the new cultivar.

It was found that the new *Penstemon* plant displays the following combination of characteristics:

(a) displays an upright compact growth habit with strong basal branching, (b) is lacking a vernalization requirement for flowering, (c) forms attractive bright pink blossoms with a white throat, and (d) is well suited for providing attractive ornamentation in the landscape.

During observations to date, the plant has been found to be hardy in U.S.D.A. Hardiness Zone No. 6. No further definitive hardiness information has been obtained. Trimming of the plant tends to produce further flowering.

The new cultivar well meets the needs of the horticultural industry and can be grown to advantage as a perennial garden plant to provide colorful ornamentation. For instance, it can be grown in parks, gardens and residential settings.

Plants of the new cultivar can be readily distinguished from other *Penstemon* cultivars including its parents. More specifically, 'Rondo' exhibits a considerably taller growth habit, and 'Navigator' commonly displays a mix of colored blossoms. The new cultivar additionally can be readily distinguished from the *Penstemon* 'Novapenpur' cultivar (U.S. Plant patent application Ser. No. 13/998,817, filed Dec. 11, 2013) through an inspection of the blossoms. More specifically, the 'Novapenpur' variety forms dissimilar dark-purple blossoms.

When compared to the 'Hot Pink' cultivar (U.S. Plant Pat. No. 23,089), the new cultivar displays considerably more basal branching.

The rooting of cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

Rooting commonly commences in approximately 23 days on average with a rooted plant commonly being formed in approximately 29 days on average.

The new cultivar of the present invention has been named 'Novapenpin', and will be marketed under the PINK ROCK CANDY Trademark.

BRIEF DESCRIPTION OF THE PHOTOGRAPHS

The accompanying photographs illustrate typical flowering specimens of the new cultivar in color as nearly true as it is reasonably possible make the same in a color illustration of this nature. The plants had been asexually reproduced by the rooting of cuttings, and had been trimmed to induce further flowering very late in the season.

FIG. 1 illustrates the typical growth habit of an entire plant of the new cultivar while displaying blossoms and foliage. The plant was approximately one year of age and was being grown in the ground outdoors in full sun late in the season (during October 2013) at West Grove, Pa., U.S.A.

Figure 2:
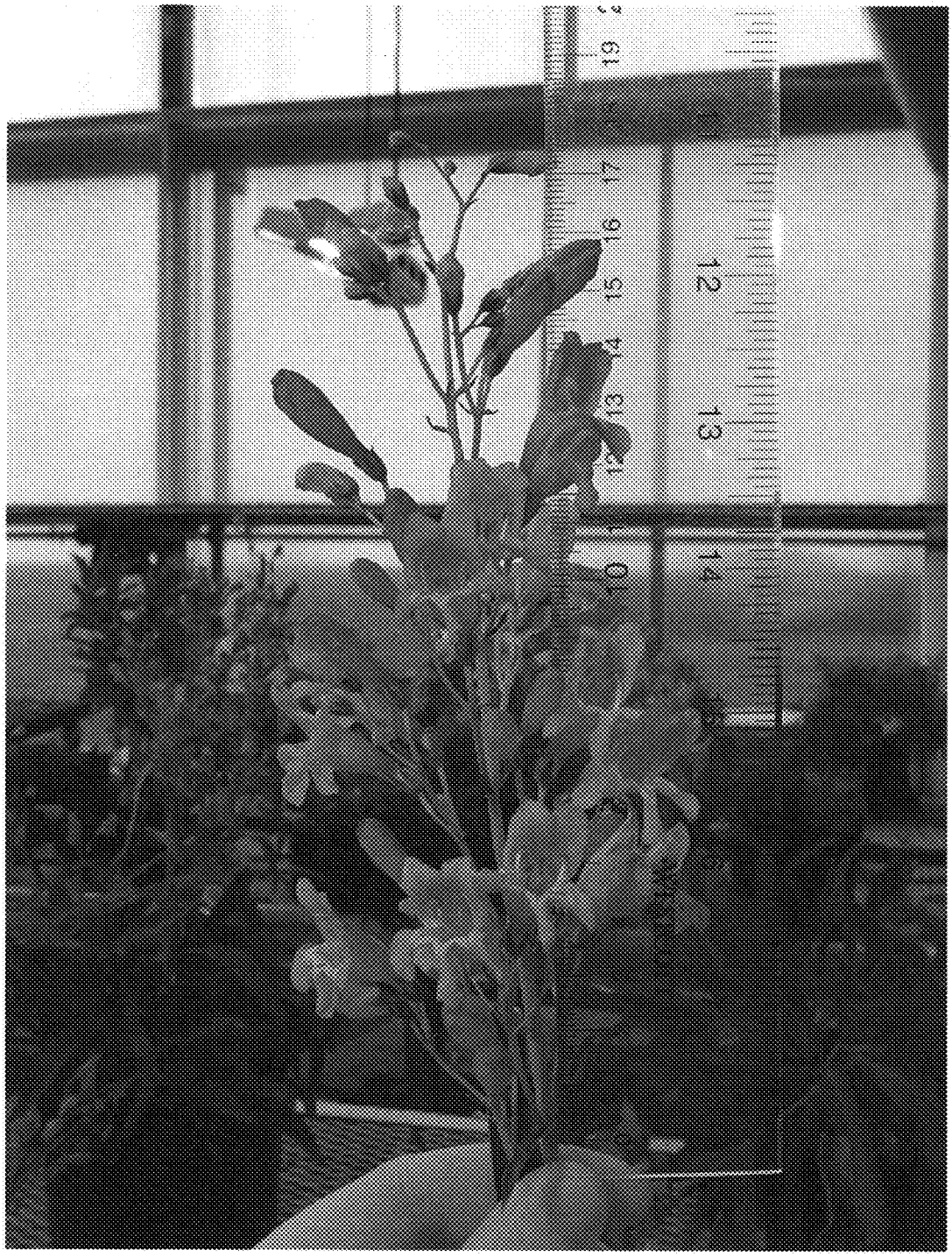

FIG. 2 illustrates a close view of an inflorescence showing the bright pink blossoms of the new cultivar in various stages of development. Dimensions in centimeters and inches are included at the right. The plant was approximately one year of age and was growing in a container under greenhouse conditions very late in the season (Nov. 2, 2015) at West Grove, Pa., U.S.A. Artificial light was utilized which contributed to the depicted brightness of the blossom coloration.

DETAILED BOTANICAL DESCRIPTION

The following is a detailed description while observing one-year-old plants of the new cultivar that were produced by the rooting of cuttings. Such plants were being grown during October 2013 in one-gallon containers under greenhouse conditions at West Grove, Pa., U.S.A. The chart used in the identification of color is The R.H.S. Colour Chart (1995 Edition or equivalent) of The Royal Horticultural Society, London, England. Common color terms are to be accorded their customary dictionary significance.

Botanical classification: *Penstemon barbatus,* cv. Novapenpin.

*Parents*.—Cross of seed mixtures of *Penstemon barbatus* 'Rondo' and 'Navigator'.

*Plant type*.—Herbaceous perennial.

Plant:

*Growth habit*.—Upright and compact.

*Height*.—Approximately 12 to 18 cm on average when mature. During observations, the 'Rondo' parent assumed a height of approximately 24 inches.

*Spread*.—Approximately 12 to 18 inches on average when mature.

*Branching*.—Commonly approximately 11 lateral stems arise at the base. During observations, this compares to approximately 2 or 3 basal branches for the 'Hot Pink Riding Hood' cultivar.

*Branch length*.—Commonly approximately 17 cm on average.

*Branch diameter*.—Commonly approximately 2 mm on average.

*Branch strength*.—Relatively strong.

*Branch texture*.—Relatively strong.

*Stem strength*.—Relatively strong.

*Stem color*.—Near Green Group 143C.

*Stem texture*.—Smooth.

*Internode length*.—Commonly approximately 2 cm.

*Roots*.—Fibrous network, and near Yellow-White Group 158C in coloration.

Foliage:

*Arrangement*.—Opposite, sessile.

*Shape*.—Broadly lanceolate.

*Apex*.—Truncate.

*Base*.—Acuminate.

*Length*.—Commonly approximately 6.5 cm on average.

*Width*.—Commonly approximately 1.3 cm on average.

*Texture*.—Smooth on the upper and under surfaces.

*Color*.—On the upper surface near Green Group 137A, and on the lower surface near Green Group 137C.

*Margins*.—Entire.

*Venation*.—Pinnate.

Inflorescence:

*Season*.—The natural flowering season for the most abundant flowering when grown outside commonly is primarily May to July in Pennsylvania, U.S.A. Less abundant flowering commonly occurs later in the season. The flowering season can be further extended with trimming.

*Type*.—Single, bi-labiate, arranged on terminal racemes, and with flowers mostly facing outwards.

*Buds*.—Ovoid, approximately 2 cm in length on average just before opening, approximately 9 mm in diameter, and near Red-Purple Group 63B in coloration.

*Quantity*.—Free-flowering, commonly with approximately 70 flowers on average developing per inflorescence.

*Inflorescence length*.—Commonly approximately 18 cm on average.

*Inflorescence width*.—Commonly approximately 9 com on average.

*Flower diameter*.—Approximately 2.2 cm on average.

*Flower depth*.—Approximately 2 cm on average.

*Petal number*.—Five.

*Petal arrangement*.—Petals fused into a tube, bi-labiate, upper lip with two upper petals, and lower lip with three lower petals.

*Petal length*.—Approximately 1 cm on average.

*Petal width*.—Approximately 7 mm on average.

*Petal shape*.—Substantially round.

*Petal apex*.—Rounded.

*Petal margin*.—Entire.

*Petal texture*.—Smooth on upper and under surfaces.

*Petal color*.—Upper surface: when opening near Red-Purple Group 63B, and when fully open near Red-Purple Group 68A. Lower surface: when opening near Red-Purple Group 63A, and when fully open near Red-Purple Group 68A.

*Throat color*.—The tube commonly is near White Group 155A.

*Longevity*.—Commonly approximately 7 days on average and influenced by environmental conditions.

*Sepal arrangement*.—Five sepals in a single whorl, and with a salverform calyx.

*Sepal shape*.—Lanceolate.

*Sepal length*.—Approximately 5 mm on average.

*Sepal diameter*.—Approximately 2 mm on average.

*Sepal apex*.—Pointed.

*Sepal base*.—Truncate.

*Sepal margin*.—Entire.

*Sepal texture*.—Smooth on upper and under surfaces.

*Sepal color*.—Near Green Group 138A on the upper surface and near Green Group 143A on the under surface.

*Stamen number*.—Four.

*Anther opening*.—Tend to dehisce the full length across the connective and to spread widely apart.

*Anther shape*.—Commonly disposed substantially horizontally on filaments.

*Anther length*.—Approximately 3 mm on average.

*Anther width*.—Less than 1 mm.

*Anther color*.—Near Greyed-Yellow Group 161B.

*Filaments*.—Commonly approximately 2.1 cm in length on average, and near White Group 155D in coloration.

*Pollen*.—Present in a moderate quantity, and near Greyed-Orange Group 164B in coloration.

*Pistil number*.—One.

*Pistil length*.—Approximately 1.5 cm on average.

*Pistil diameter*.—Approximately 1 mm on average.

*Style length*.—Approximately 1.3 cm on average.

*Style color*.—Near White Group 155D at the apex and base, commonly with some Red-Purple Group 70B at the center portion.

*Stigma shape*.—Substantially round.

*Stigma color*.—Near White Group 155D.

*Ovary color*.—Near Yellow-Green Group 144C.

*Seeds/fruit*.—Have not been observed.

*Fragrance*.—None detected.

*Peduncle length*.—Approximately 1.5 to 2 cm on average.

*Peduncle diameter*.—Approximately 2 mm on average.

*Peduncle aspect*.—Commonly approximately 80 degrees.

*Peduncle texture*.—Smooth.

*Peduncle strength*.—Relatively strong.

*Peduncle color*.—Near Yellow-Green Group 145A.

*Pedicel length*.—Approximately 5 to 6 mm on average.

*Pedicel diameter*.—Approximately 1 mm on average.

*Pedicel aspect*.—Commonly approximately 45 degrees.

*Pedicel texture*.—Smooth.

*Pedicel strength*.—Relatively strong.

*Pedicel color*.—Near Yellow-Green Group 145A.

Disease resistance: The tolerance/susceptibility to diseases and pests common to *Penstemon* plants appears to be typical during observations to date.

Plants of the 'Novapenpin' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Penstemon* plant having the following combination of characteristics:

(a) displays an upright compact growth habit with strong basal branching, (b) is lacking a vernalization requirement for flowering, (c) forms attractive bright pink blossoms with a white throat, and (d) is well suited for providing attractive ornamentation in the landscape;

substantially as illustrated and described.

* * * * *